(12) United States Patent
Eggleston

(10) Patent No.: US 6,258,085 B1
(45) Date of Patent: Jul. 10, 2001

(54) ELECTROSURGICAL RETURN ELECTRODE MONITOR

(75) Inventor: Jeffrey L. Eggleston, Broomfield, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/310,059

(22) Filed: May 11, 1999

(51) Int. Cl.$^7$ .................................................. A61B 18/04
(52) U.S. Cl. ................................. 606/35; 606/38; 606/42
(58) Field of Search .................................. 606/32, 34, 35, 606/37, 38–42, 46–50; 607/115, 116

(56) References Cited

U.S. PATENT DOCUMENTS

| 3,683,923 | 8/1972 | Anderson . |
| --- | --- | --- |
| 3,913,583 | 10/1975 | Bross . |
| 4,094,320 | 6/1978 | Newton et al. . |
| 4,121,590 | 10/1978 | Gonser . |
| 4,303,073 | 12/1981 | Archibald . |
| 4,343,308 | 8/1982 | Gross . |
| 4,416,276 | 11/1983 | Newton et al. . |
| 4,416,277 | 11/1983 | Newton et al. . |
| 4,437,464 | 3/1984 | Crow . |
| 4,494,541 | 1/1985 | Archibald . |
| 4,657,015 | 4/1987 | Irnich . |
| 4,658,819 | * 4/1987 | Harris et al. ........................ 606/35 |
| 4,741,334 | 5/1988 | Irnich . |
| 5,480,399 | 1/1996 | Hebborn . |
| 5,496,312 | 3/1996 | Klicek . |
| 5,695,494 | 12/1997 | Becker . |
| 5,766,165 | 6/1998 | Gentelia et al. . |
| 5,797,902 | 8/1998 | Netherly . |
| 5,976,128 | 11/1999 | Schilling et al. . |
| 6,053,910 | 4/2000 | Fleenor . |

* cited by examiner

Primary Examiner—Linda C. M. Dvorak
Assistant Examiner—R. Kearney

(57) ABSTRACT

The present disclosure provides a method for determining the probability of a patient burn under a return electrode in a momopolar electrosurgical system comprising calculating a heating factor adjacent the return electrode utilizing a first algorithm, calculating a cooling factor adjacent the return electrode utilizing a second algorithm, subtracting the calculated cooling factor from the calculated heating factor to obtain a difference value, comparing the difference value to a threshold value, and adjusting the power dependent on the relationship of the difference value to the threshold value.

9 Claims, 3 Drawing Sheets

FIG_1

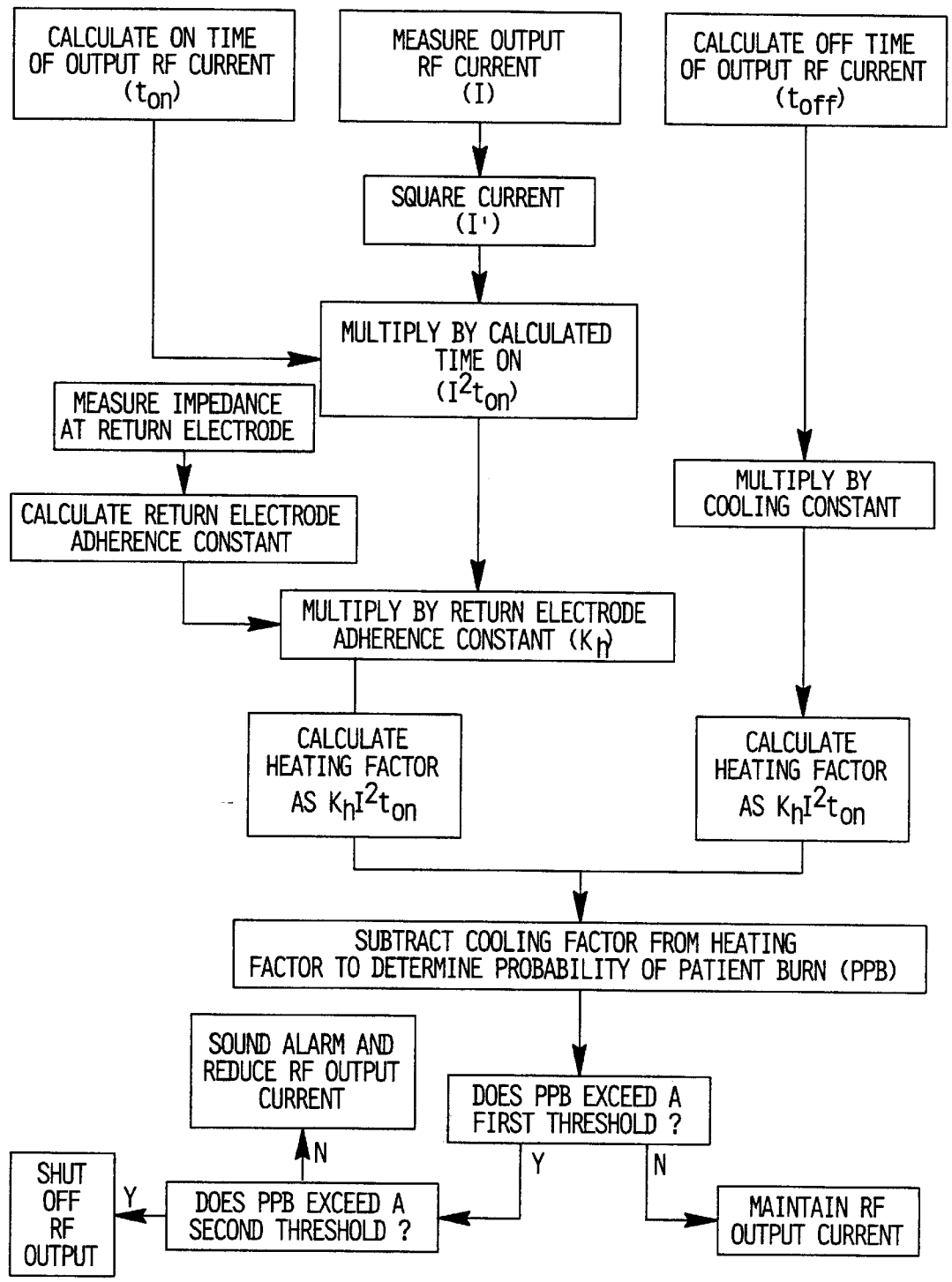
FIG_3

ELECTROSURGICAL RETURN ELECTRODE MONITOR

BACKGROUND

1. Technical Field

This application relates to an apparatus and method for determining the probability of patient burn during electrosurgery, and more particularly to determining the probability of patient burn under a return electrode in a monopolar electrosurgical system.

2. Background of Related Art

During electrosurgery, a source or active electrode delivers energy, such as radio frequency energy, to the patient and a return electrode carries the current back to the electrosurgical generator. In monopolar electrosurgery, the source electrode is typically the hand-held instrument placed by the surgeon at the surgical site and the high current density flow at this electrode creates the desired surgical effect of cutting or coagulating tissue. The patient return electrode is placed at a remote site from the source electrode and is typically in the form of a pad adhesively adhered to the patient.

The return electrode has a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce heat intensity. Return electrodes are sized based on assumptions of the maximum current seen in surgery and the duty cycle (the percentage of time the generator is on) during the procedure. The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and in turn increasing the heat applied to the tissue. This risked burning the patients in the area under the adhered portion of the return electrode if the tissue was heated beyond the point where the circulation could cool the skin.

To address this problem, split return electrodes and hardware circuits, generically called Return Electrode Contact Quality Monitors (RECQMs), were developed. These split electrodes consist of two separate conductive foils. The hardware circuit uses an AC signal between the two electrode halves to measure the impedance therebetween. This impedance measurement is indicative of how well the return electrode is adhered to the patient since the impedance between the two halves is directly related to the area of patient contact. That is, if the electrode begins to peel from the patient, the impedance increases since the contact area of the electrode decreases. Current RECQMs are designed to sense this change in impedance so that when the percentage increase in impedance exceeds a predetermined value or the measured impedance exceeds a threshold level, the electrosurgical generator is shut down to reduce the chances of burning the patient Although monitoring circuits in present use are effective, they do not take into account the amount of time the current is being delivered. As new surgical procedures continue to be developed that utilize higher current and higher duty cycles, increased heating of tissue under the return electrode will occur. It would therefore be advantageous to design a monitoring circuit which would also factor in the amount of time the current is being delivered in determining the probability of a patient burn. Based on this probability determination, an alarm signal can be generated or power supplied from the generator can be shut off.

U.S. Pat. No. 4,657,015 discloses a control device for cutting off high frequency current during electrosurgery if the heat buildup in the body tissue exceeds a predetermined value. In the '015 patent, a control electrode is affixed to the body spaced from the active electrode and separate from the neutral (return) electrode. The control electrode is designed to pick up the voltage existing on the body. The voltage signal is squared, integrated over time and compared to a reference voltage. The high frequency generator is turned off if the voltage value exceeds the reference voltage. The '015 patent does not effectively measure heating under the return electrode since the measurements are calculated by a separate control electrode. The '105 patent even states that the effective surface area of the neutral electrode is not a factor in the heat calculations. Also, the amount of time the energy is being applied is not a factor in the heat calculations. Additionally, the '015 patent uses voltage measurement to determine overheating of tissue. It is currently believed by the inventors of this application that current measurement provides a more accurate parameter because voltage values actually measure the ability to transfer energy through the tissue while current values measure actual heating of the tissue.

U.S. Pat. No. 4,741,334 discloses a control circuit intended to reduce burning of tissue. As in the '015 patent, a separate control electrode is provided to determine the body voltage. The control electrode is spaced from the neutral electrode and functions to detect a high frequency body surface voltage. The body surface voltage is converted into dc voltage by a converter and inputted to a comparator for comparison to a reference voltage. The generator is turned off if the body voltage exceeds the reference voltage. The '015 patent also discloses a monitor circuit for testing whether the neutral electrode is in good contact with the body surface of the patient. A comparator compares the body surface voltage detected by the control electrode with a reference voltage derived from the operational voltage of the surgical device. An audible signal is produced when these voltage values reach a predetermined ratio. Similar to the '015 patent, the '334 patent requires an additional electrode, measures voltage instead of current to determine overheating, and does not factor in the amount of time the high frequency energy is being applied.

As noted above, it would be advantageous to provide a monitoring circuit which effectively determines the probability of overheating tissue, i.e. the probability of patient burn, by measuring current and factoring in the time period of energy delivery of energy.

SUMMARY

The present disclosure provides a method for determining the probability of a patient burn under a return electrode in a monopolar electrosurgical system comprising calculating a heating factor adjacent the return electrode utilizing a first algorithm, calculating a cooling factor adjacent the return electrode utilizing a second algorithm, subtracting the calculated cooling factor from the calculated heating factor to obtain a difference value, comparing the difference value to a threshold value, and adjusting the power dependent on the relationship of the difference value to the threshold value.

The step of calculating the cooling factor preferably comprises the steps of calculating the off time of the output current to obtain an off time value and multiplying the off time value by a first constant indicative the body's ability to remove heat. The step of calculating the heating factor preferably comprises the steps of multiplying the square of the output current by a second constant indicative of the measured impedance at the return electrode, the second constant being representative of the adherence of the return electrode to the patient, and multiplying the product by the on time value of the output.

The method preferably comprises the step of generating an alarm if the difference value exceeds the threshold value. The step of adjusting the power includes the step of shutting off the power if the difference value exceeds a second threshold value (a predetermined value) and reducing the power if the difference value is below the second threshold value.

The present disclosure also provides a method for determining the probability of a patient burn in a monopolar electrosurgical system comprising calculating a heating factor adjacent the return electrode utilizing a first algorithm, calculating a cooling factor adjacent the return electrode utilizing a second algorithm, subtracting the calculated cooling factor from the calculated heating factor to obtain a difference value, comparing the difference value to a threshold value, and generating a warning signal if the difference value exceeds the predetermined value.

The first algorithm includes multiplying a current value, obtained by squaring the measured output current, by a constant indicative of the measured impedance at the return electrode and by the on time value of the output current. The second algorithm includes multiplying the off time of the output current by a constant indicative by the ability of the body to remove heat.

The present disclosure further provides an electrosurgical generator for use in a monopolar electrosurgical system having an electrosurgical tool for treating tissue, a return electrode, and an impedance sensor in electrical communication with the return electrode to measure impedance of the return electrode. The electrosurgical generator comprises a current sensor for measuring the output current delivered by the generator and a microprocessor electrically connected to the current sensor and the impedance sensor for calculating the heating factor and cooling factor under the return electrode wherein the calculation of the heating factor is based at least in part on the measured output current. The generator also includes a controller electrically connected to the microprocessor for adjusting the power supply of the generator in response to the relationship of the calculated heating and cooling factors. The microprocessor includes a first algorithm for calculating the heating factor and a second algorithm for calculating the cooling factor. The first algorithm is defined as:

$$K_h I^2 t_{on}$$

wherein $K_h$ is the constant related to the contact impedance in Ohms of the return electrode, $I^2$ is the square of the output current in milliamps and $t_{on}$ is the time in seconds that the output current is delivered.

The second algorithm is defined as:

$$K_c t_{off}$$

wherein $K_c$ is the constant representative of the time it takes for the body to cool down in degrees per minute and $t_{off}$ is the time in seconds that the output current is not being delivered.

The microprocessor also includes an algorithm for subtracting the cooling factor from the heating factor to calculate a difference value, and the generator further comprises a comparator electrically connected to the microprocessor for comparing the difference value to a threshold value. The comparator is electrically connected to a controller to generate a first signal indicative of the relationship of the difference value and the threshold value. An alarm is electrically connected to the comparator for generating a warning signal if the difference value exceeds the threshold value by a predetermined amount. The controller generates a shut off signal to terminate power if the difference value exceeds a predetermined value (the second threshold), the predetermined value being greater than the threshold value, and the controller generates a second signal to reduce the power if the difference value exceeds the threshold value, but is less than the predetermined value.

DETAILED DESCRIPTION OF THE DRAWINGS

Preferred embodiments of the present disclosure are described herein with reference to the drawings wherein:

FIG. 3 is a flow diagram showing the steps followed for calculating the probability of patient burn and for controlling the output current.

DETAILED DESCRIPTION OF THE PREFERRED EMBODIMENTS

Figure 1:
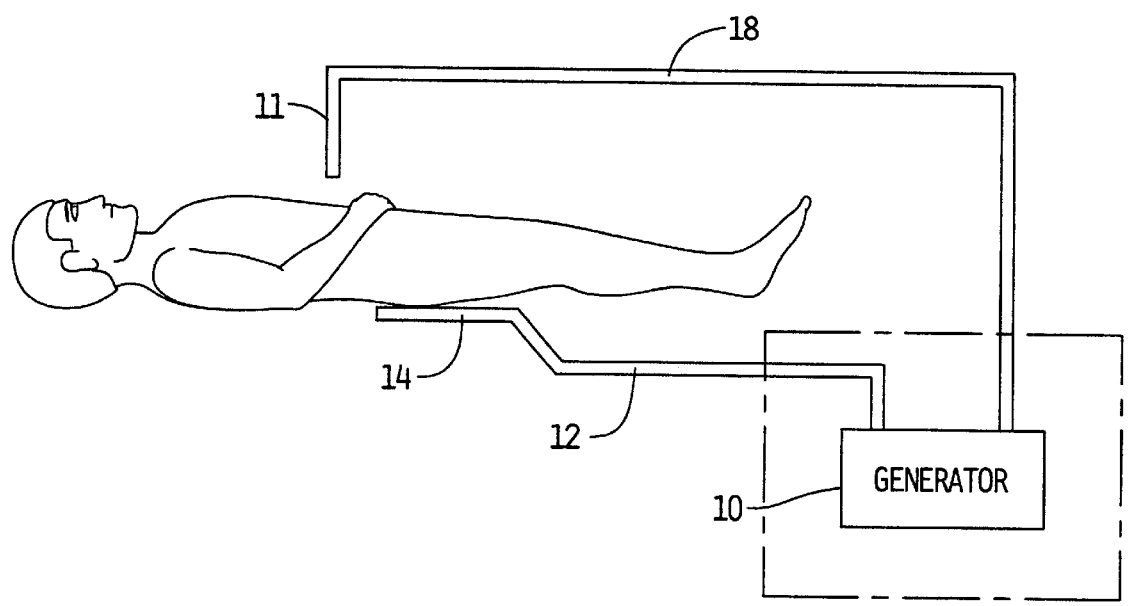
FIG. 1 is a schematic illustration of a monopolar electrosurgcial system.

FIG. 1 is a schematic illustration of a monopolar electrosurgical system. The surgical instrument for treating tissue at the surgical site is designated by reference numeral 11. Electrosurgical energy is supplied to instrument 11 by generator 10 via cable 18 to cut, coagulate, etc. tissue. A return electrode, designated by reference numeral 14, is shown placed under the patient to return the energy from the patient back to the patient via wire 12. The return electrode is preferably in the form of a split pad which is adhesively attached to the patient's skin.

The area of the return electrode that adheres to the patient is important since it affects the current density of the signal that heats the tissue. The smaller the contact area of the return electrode with the patient's tissue, the greater the current density and the greater and more concentrated is the heating of tissue. Conversely, the greater the contact area of the return electrode, the smaller the current density and the less heating of the tissue. Obviously, the greater the heating of the tissue, the greater the probability of burning the tissue.

Figure 2:
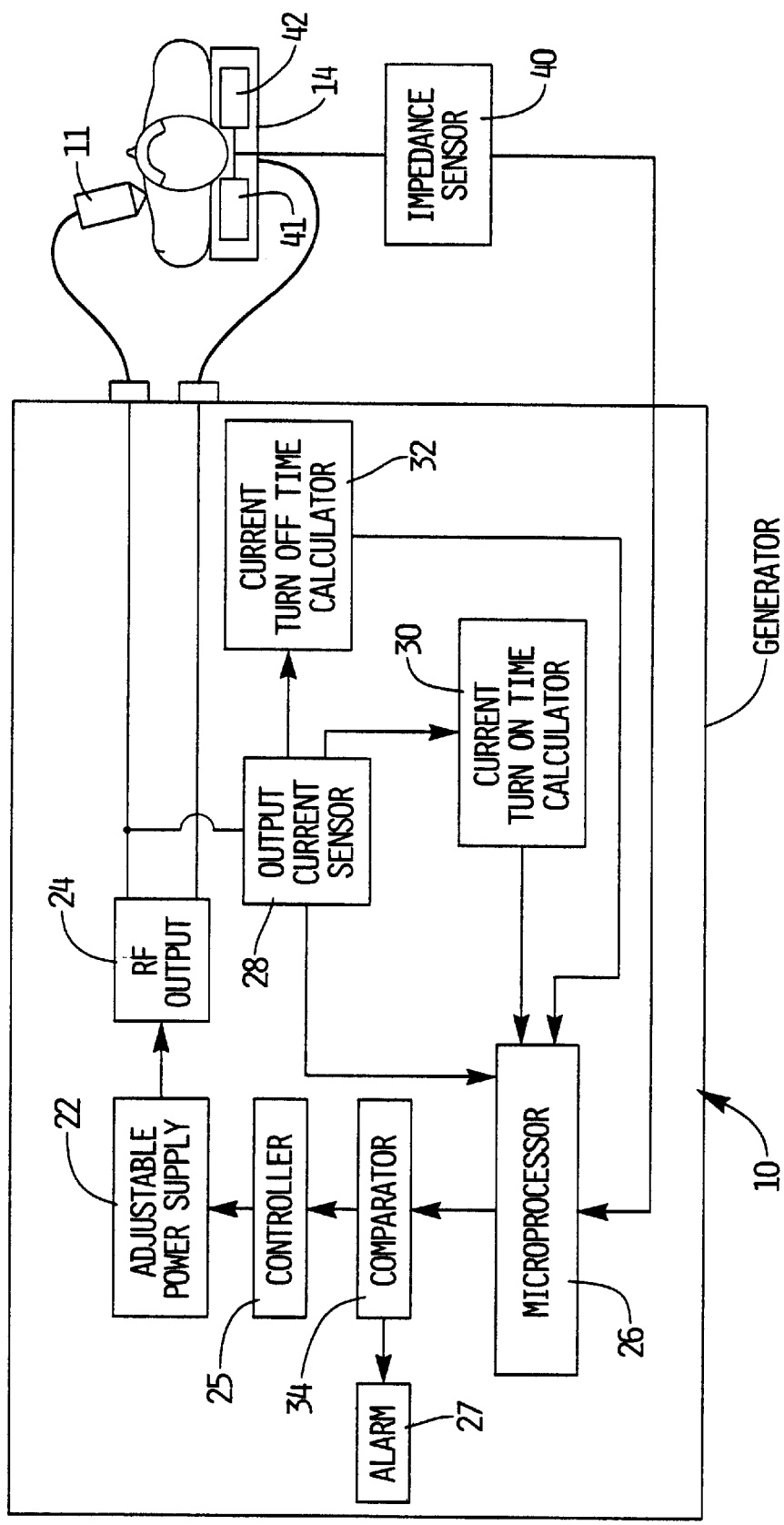
FIG. 2 is a schematic block diagram of the electrosurgical system for determining the probability of patient burn.

FIG. 2 illustrates a conventional return electrode that is split to enable the impedance to be measured between the two halves. The impedance measurement provides an indication of how well the return electrode is adhered to the patient since there is a direct relationship between the impedance and the area of patient contact. If the electrode is partially peeled from the patient, the impedance increases. This is because each portion, e.g. square centimeter, of the electrode pad that touches the patient has a resistance of its own. All of these resistances are in parallel, and the resultant equivalent resistance is smaller than any of the individual elements. If any of these parallel resistances are removed because of peeling, the equivalent resistance increases slightly. Return Electrode Contact Quality Monitors (RECQMs) utilize an AC signal between the two electrode halves to measure impedance between them. The diagram of FIG. 2 schematically depicts this function of the RECQM.

If the total current passed through the return electrode is increased or the current duty cycle, defined by the percentage of time the generator is on and the current is applied, is increased, heating under the electrode will increase.

The heating factor of the tissue is a measure of how much heat is dissipated in the tissue. The following equation provides the heating factor:

Heating Factor=$I^2 t_{on}$ where $I^2$ equals the current in milliamps, and $t_{on}$ equals the time the RF generator is on in seconds.

Thus, the heating factor can be defined as the square of a given current passed through the return electrode attached to a patient multiplied by the time the current is applied. As is apparent from the equation, if either the current is increased or the on time is increased, the amount of heat dissipated in the tissue, and thus the chances of patient burn, are increased.

The foregoing heat factor equation assumes that the area attached to the patient is unchanged. However, as a practical matter, that area can change as a portion of the return electrode can become detached from the patient. To accommodate for changed surface contact area of the return electrode, a constant $K_h$ is added to the equation where $K_h >= 1$. This can be modeled by the following equation:

Heating Factor=$K_h I^2 t_{on}$ where $K_h=1$ when the return electrode is fully adhered, and $K_h>1$ if the return electrode is not fully adhered.

Therefore, as is apparent from the equation, if the surface contact area of the return electrode decreases, since $K_h$ will be greater than 1, the heating factor will increase. As the surface area decreases, as explained above, the current density increases and the amount of heating for a given output current also increases.

Another factor affecting dissipation of heat in the tissue is the time period the RF energy is applied. The patient's body has the ability to remove heat from the area under the return electrode by the blood flow in the capillaries, small arteries and small veins. The more time between the applications of RF energy, the greater the heat removal because the body will have more time to naturally remove the heat. This ability to remove heat over a period of time can be modeled by the following equation:

Cooling factor=$K_c t_{off}$ where KC is a cooling constant dependent on the patient and $t_{off}$ is the time in seconds that the RF energy is off During electrosurgery, the RF generator goes on and off many times. The conventional Return Electrode Contact Quality Monitor (RECQM) determines if the return electrode is attached to the patient by measuring the impedance. However, if a high current or a high duty cycle is utilized, a burn can still occur because the body may not be able to remove the heat fast enough.

The present disclosure not only measures the current delivered and the time period the current is delivered, but calculates and compares the heating and cooling factors in order to measure the probability of a patient burn.

More particularly, and with reference to FIG. 2, the electrosurgical generator includes a microprocessor 26, an adjustable power supply 22, such as a high voltage supply, for producing RF current, and an RF output stage 24 electrically connected to the power supply 22 for generating an output voltage and output current for transmission to the instrument 11. The power supply is adjusted by controller 25 dependent on the calculated probability of patient burn which is described in detail below.

The microprocessor 26 has a plurality of input ports. One input port is in electrical communication with the output current sensor 28 which measures the output current of the RF output stage 24 being transmitted to the patient. The second input port is electrically connected to the current turn on time calculator 30. During the surgical procedure, the generator is activated at set or varying time intervals, with intermittent shut down time intervals to allow the tissue to naturally cool as the patient's blood flow dissipates heat. The calculator 30 determines the amount of the time the current is being supplied and transmits a signal representative of this calculated time to the microprocessor 26. The current turn off time calculator 32 sends a signal to the microprocessor 26 via one of its input ports representative of the time the RF output current has been turned off.

An algorithm in the microprocessor 26, described in more detail below, processes the signals from the current sensor 28 and the time calculators 30 and 32 in the calculation of the probability of patient burn. The output port of the microprocessor 26 is in electrical communication with comparator 34. The calculation of microprocessor 26 is compared to threshold values supplied to or present in the comparator 34, and if these values are exceeded, an alarm signal is sent to generate an alarm as a warning to the user. If the threshold values are exceeded, the comparator 34 also sends a power adjustment signal to the controller 25 which signals the power supply 22 to either adjust, e.g. reduce the RF output current, or shut off the power supply 22 to terminate the supply of current, dependent on the amount the threshold is exceeded.

An impedance sensor 40 forms part of the return electrode circuit. The sensor 40 measures the impedance between the split pads 41,42 of the return electrode pad 44 to determine the degree of adherence of the electrode pad 44. That is, if a portion of the electrode pad 44 becomes detached from the patient, the impedance will increase. The sensor 40 transmits a signal indicative of the measured impedance to an input port of the microprocessor 26. The microprocessor algorithm factors in the impedance measurement in the manner described below.

Turning now to FIG. 3, the algorithm for calculating the probability of patient burn (hereinafter "PPB") and the system for adjusting the RF output current is illustrated in flow diagram. As shown, output of the RF current is measured and squared, represented by $I^2$ in mlliamps. The time the RF current is being applied ($t_{on}$), measured in seconds, is multiplied by the squared current, the formula being represented by $I^2 t_{on}$ to yield a first value.

As discussed above, the impedance sensor 40 measures the impedance at the return electrode which is indicative of the degree of adherence of the return electrode to the patient to thereby provide an adherence constant $K_h$. This adherence constant is multiplied by $I^2 t_{on}$ to calculate the heating factor. Thus, the heating factor is calculated by the algorithm $K_h I^2 t_{on}$ wherein $K_h$ is the adherence constant and K=1 when the return electrode is fully adhered to the patient and K>1 if the electrode is not fully adhered.

The cooling factor is calculated by the measured time the current is not being applied. More specifically, the time off in seconds of the output current ($t_{off}$) is calculated, and multiplied by the cooling constant $K_c$ to calculate the cooling factor as $K_c t_{off}$. The cooling constant $K_c$ takes into account that the blood flow in the capillaries, small arteries and veins of the patient cools the tissue over time. For example, assuming tissue normally cools at 1 degree per minute, since there is some variation, the cooling constant could be conservatively selected as ½ degree per minute. Other constants could be selected depending on the tissue cooling time.

With continued reference to the flow diagram of FIG. 3, the cooling factor is subtracted from the heating factor by the microprocessor to determine a value (a "difference value") representative of the probability of patient burn. ("PPB"). After this calculation in the microprocessor, the microprocessor 26 sends a signal to the comparator 34 representative of the difference value (see also FIG. 2), where the difference value is compared to a first threshold value. If the difference value is less than or equal to the first threshold value, a signal sent to the controller and in turn to the power supply maintains the RF output current. That is, if the difference value is less than or equal to the threshold value, this indicates that the differential between the cooling factor and heating factor is relatively low, indicating a low probability of patient burn, and no adjustments need to be made.

On the other hand, if the difference value exceeds the first threshold value, the value is then compared by the comparator 34 to a second threshold (predetermined) value. The second threshold value is preset to correspond to the situation where a patient burn is highly likely and the RF current through the tissue needs to be terminated. If the difference value exceeds the second threshold value, this indicates that the heating factor is too high relative to the cooling factor. The comparator 34 will transmit a second signal to the controller 25. The controller 25 will process this signal and generate a shut off signal to the power supply 22 to shut off the RF current. This shut off will allow the body time to dissipate the heat and cool the tissue. However, if the difference value exceeds the first threshold value, but does not exceed the second threshold value, this means that although the heating factor is relatively high and the probability of patient burn likely at the current power levels it is not high enough that a shut down is mandated. Instead, the output level needs to be reduced. In this circumstance, the comparator 34 will transmit a third signal to the controller 25 indicative of the high PPB value. The controller 25 in turn will transmit a signal to the power supply 22 (see FIG. 2) to reduce the output power to thereby reduce the output current by a preset amount. Thus, the system remains on, but at reduced current levels, to reduce the heating affect on the tissue. As is apparent, by reducing the current output, the heating factor will be reduced since the heating factor is calculated in part by the square of the current. By reducing the heating factor, the differential between the heating factor and cooling factor is reduced, thus reducing the value of the probability of patient burn. The PPB is preferably continuously calculated in this manner throughout the surgical procedure in order to continuously monitor and control the heating of tissue.

As indicated in FIGS. 2 and 3, if the probability of patient burn exceeds the first threshold value an alarm signal is sent to alarm 27 to generate an alarm. The alarm can be in the form of a visual indicator, and audible indicator or both. Additionally, a visual and/or audible alarm can be sounded if the PPB exceeds the second threshold value indicating shut off of the power supply.

In summary, the following formulas explain the responses to PPB values:

If first threshold value<difference value and second threshold value<difference value, then shut off RF output current;

If first threshold value<difference value<second threshold value, then adjust RF current supply; and If first threshold value>difference value, then maintain RF output current.

It is also contemplated that if the difference value falls between the first threshold value and the second threshold value, rather than reducing the power, the duty cycle can be reduced. This can be accompanied by an audible or visible indicator. The duty cycle reduction could also alternately be the first response if the PPB exceeds a first threshold followed by a reduction in power if the first threshold is further exceeded.

Both threshold values are predetermined based on the probability of patient burn so the overheating of tissue can be timely detected and the electrosurgical generator adjusted accordingly. Using current values as part of the heating factor calculation is believed to increase the accuracy of the PPB determination since current values are believed to actually cause the heating of the tissue.

In an alternate embodiment, the method includes the additional step of determining the size of the return electrode to be utilized, e.g. adult, infant, neonate, and adjusting the heating and cooling constants accordingly. The user could inform the generator of the size being used or alternatively the size can be automatically sensed by the generator based on the differences in the electrode connector.

While the above description contain many specifics, those specifics should not be construed as limitations on the scope on the disclosure, but merely as exemplifications of preferred embodements thereof. These skilled in the art will envision many other possible variations that are within the scope and spirit of the disclosure as defined by the claims appended hereto.

What is claimed is:

1. An electrosurgical system comprising:
    an electrosurgical generator having an electrosurgical tool for treating tissue,
    a return electrode, and
    an impedance sensor in electrical communication with the return electrode to measure impedance of the return electrode,
    wherein said electrosurgical generator further comprises:
        a current sensor for measuring an output current delivered by the electrosurgical generator;
        a microprocessor electrically connected to the current sensor and the impedance sensor for calculating a heating factor and a cooling factor of the tissue under the return electrode, the calculation of the heating factor being based at least in part on the measured output current; and
        a controller electrically connected to the microprocessor for adjusting a power supply of the generator in response to a relationship of the calculated heating and cooling factors.

2. The generator of claim 1, wherein the microprocessor includes a first algorithm for calculating the heating factor and a second algorithm for calculating the cooling factor.

3. The generator of claim 2, wherein the second algorithm is defined as $$k_c t_{off}$$

wherein $K_c$ is a constant representative of the time it takes for the tissue to cool down in degrees per minute and $t_{off}$ is the time in seconds that the output current is not being delivered.

4. The generator of claim 2, wherein the first algorithm is defined as $$k_h I^2 t_{on}$$

wherein $K_h$ is a constant representative of a measured impedance in Ohms of the return electrode, $I^2$ is the square of said measured output current in milliamps and $t_{on}$ is the time in seconds that the output current is delivered.

5. The generator of claim 4, wherein the measured impedance is indicative of the degree of adherence to the tissue of the return electrode.

6. The electrosurgical generator of claim 1, wherein the microprocessor includes an algorithm for subtracting the cooling factor from the heating factor to calculate a difference value, and the generator further comprises a comparator electrically connected to the microprocessor for comparing the difference value to a threshold value, the comparator being electrically connected to the controller to generate a first signal indicative of the relationship of the difference value and the threshold value.

7. The electrosurgical generator of claim 6, further comprising an alarm electrically connected to the comparator for generating a warning signal if the difference value exceeds the threshold value by a predetermined amount.

8. The electrosurgical generator of claim 6, wherein the controller generates a shut off signal to terminate power if the difference value exceeds a predetermined value, the predetermined value being greater than the threshold value.

9. The electrosurgical generator of claim 8, wherein the controller generates a second signal to reduce the power if the difference value exceeds the threshold value but does not exceed the predetermined value.

* * * * *